US012065627B2

(12) United States Patent
Tan et al.

(10) Patent No.: US 12,065,627 B2
(45) Date of Patent: Aug. 20, 2024

(54) MULTILAYER DISSOLVABLE SOLID ARTICLE WITH APERTURES OR HOLES

(71) Applicant: The Procter & Gamble Company, Cincinnati, OH (US)

(72) Inventors: Hongsing Tan, Beijing (CN); Carl David MacNamara, Beijing (CN)

(73) Assignee: The Procter & Gamble Company, Cincinnati, OH (US)

( * ) Notice: Subject to any disclaimer, the term of this patent is extended or adjusted under 35 U.S.C. 154(b) by 150 days.

(21) Appl. No.: 17/368,898

(22) Filed: Jul. 7, 2021

(65) Prior Publication Data

US 2023/0008032 A1 Jan. 12, 2023
US 2024/0117281 A9 Apr. 11, 2024

Related U.S. Application Data

(63) Continuation of application No. PCT/CN2019/071781, filed on Jan. 15, 2019.

(51) Int. Cl.
*C11D 17/06* (2006.01)
*C11D 1/37* (2006.01)
*C11D 3/20* (2006.01)
*C11D 3/37* (2006.01)
*C11D 11/00* (2006.01)
*C11D 1/14* (2006.01)
*C11D 1/29* (2006.01)

(52) U.S. Cl.
CPC .............. *C11D 17/06* (2013.01); *C11D 1/37* (2013.01); *C11D 3/2065* (2013.01); *C11D 3/3753* (2013.01); *C11D 1/146* (2013.01); *C11D 1/29* (2013.01); *C11D 2111/12* (2024.01)

(58) Field of Classification Search
CPC ......... C11D 17/06; C11D 1/37; C11D 3/2065; C11D 11/0017
See application file for complete search history.

(56) References Cited

U.S. PATENT DOCUMENTS

| | | |
|---|---|---|
| 3,528,434 A | 9/1970 | Halter et al. |
| 4,170,565 A | 10/1979 | Flesher et al. |
| 4,557,852 A | 12/1985 | Schulz et al. |
| 4,610,799 A | 9/1986 | Wilsberg et al. |
| 4,654,395 A | 3/1987 | Schulz et al. |
| 4,699,976 A | 10/1987 | Matsubara et al. |
| 4,743,394 A | 5/1988 | Kaufmann et al. |
| 4,747,976 A | 5/1988 | Yang et al. |
| 4,806,261 A | 2/1989 | Ciallella et al. |
| 4,938,888 A | 7/1990 | Kiefer et al. |
| 5,202,045 A | 4/1993 | Karpusiewicz et al. |
| 5,278,379 A | 1/1994 | Takanashi |
| 5,393,528 A | 2/1995 | Staab |
| 6,465,407 B2 | 10/2002 | Hayashi |
| 6,699,826 B1 | 3/2004 | Saijo |
| 6,818,606 B1 | 11/2004 | Hanada |
| 7,094,744 B1 | 8/2006 | Kobayashi |
| 8,268,764 B2* | 9/2012 | Glenn, Jr. ............. A61K 8/11 510/141 |
| 8,367,596 B2 | 2/2013 | Fossum et al. |
| 8,425,622 B2* | 4/2013 | Felts ................ A61K 8/416 8/405 |
| 8,461,091 B2* | 6/2013 | Glenn, Jr. .......... A61K 8/0216 510/501 |
| 8,466,099 B2 | 6/2013 | Glenn, Jr. et al. |
| 8,765,170 B2 | 7/2014 | Glenn, Jr. et al. |
| 9,233,055 B2 | 1/2016 | Glenn, Jr. et al. |
| 10,717,839 B2 | 7/2020 | Mao et al. |
| 10,752,869 B2 | 8/2020 | Tan et al. |
| 2002/0091169 A1 | 7/2002 | Klotzer |
| 2003/0024997 A1 | 2/2003 | Welch |
| 2004/0071755 A1 | 4/2004 | Fox |
| 2006/0147493 A1 | 7/2006 | Yang et al. |
| 2009/0104420 A1 | 4/2009 | Nadella et al. |
| 2010/0167971 A1* | 7/2010 | Glenn, Jr. ............. A61K 8/11 264/50 |
| 2010/0173817 A1 | 7/2010 | Glenn, Jr. et al. |
| 2011/0028374 A1* | 2/2011 | Fossum ............... C11D 3/0052 510/296 |
| 2011/0136719 A1 | 6/2011 | Jalbert |
| 2011/0189246 A1 | 8/2011 | Glenn, Jr. et al. |
| 2011/0266717 A1 | 11/2011 | Nehls et al. |
| 2011/0313072 A1 | 12/2011 | Maurer et al. |

(Continued)

FOREIGN PATENT DOCUMENTS

BR 112021013072 A2 * 9/2021 ........... A61K 8/0216
CA 1242949 A 10/1988

(Continued)

OTHER PUBLICATIONS

PCT Suppl. Search Report and Written Opinion for PCT/CN2019/071781 dated Apr. 16, 2021, 10 pages.
PCT Search Report and Written Opinion for PCT/CN2019/071781 dated Oct. 22, 2019, 11 pages.
All Office Actions; U.S. Appl. No. 17/368,884, filed on Jul. 7, 2021.
All Office Actions; U.S. Appl. No. 17/368,893, filed on Jul. 7, 2021.
All Office Actions, U.S. Appl. No. 17/368,895, filed on Jul. 7, 2021.
Unpublished U.S. Appl. No. 17/368,895, filed on Jul. 7, 2021, to Hongsing Tan et. al.

(Continued)

*Primary Examiner* — Nicole M. Buie-Hatcher
*Assistant Examiner* — M. Reza Asdjodi
(74) *Attorney, Agent, or Firm* — George H. Leal; Carrie Schwartz

(57) ABSTRACT

A dissolvable solid article is provided, which is characterized by a multilayer structure formed of two or more flexible and dissolvable sheets that each comprises a water-soluble polymer. Such dissolvable solid article is at least 2 mm thick and contains one or more through-apertures or through-holes with a width or diameter of 0.2-0.8 mm.

20 Claims, No Drawings

(56) References Cited

U.S. PATENT DOCUMENTS

| | | | |
|---|---|---|---|
| 2012/0021022 A1 | 1/2012 | Hakim | |
| 2012/0270029 A1* | 10/2012 | Glenn, Jr. | A61Q 5/02 428/221 |
| 2013/0303419 A1 | 11/2013 | Glenn, Jr. et al. | |
| 2014/0105946 A1 | 4/2014 | Glenn, Jr. et al. | |
| 2015/0159330 A1 | 6/2015 | Weisman et al. | |
| 2015/0190476 A1 | 7/2015 | Schobel et al. | |
| 2015/0218497 A1 | 8/2015 | Jalbert et al. | |
| 2015/0315350 A1* | 11/2015 | Mao | A61Q 5/12 427/180 |
| 2017/0065512 A1 | 3/2017 | Zhu et al. | |
| 2017/0137591 A1 | 5/2017 | Mukaiyama et al. | |
| 2018/0216052 A1 | 8/2018 | Denome | |
| 2018/0216053 A1 | 8/2018 | Denome | |
| 2018/0223229 A1* | 8/2018 | Tan | C11D 11/0017 |
| 2018/0320669 A1 | 11/2018 | Stack et al. | |
| 2020/0010784 A1 | 1/2020 | Cho et al. | |
| 2020/0308517 A1* | 10/2020 | Tan | A61K 8/345 |
| 2021/0163698 A1* | 6/2021 | MacNamara | C08J 9/30 |
| 2021/0332212 A1 | 10/2021 | Tan et al. | |
| 2021/0332312 A1 | 10/2021 | Tan et al. | |
| 2021/0363472 A1* | 11/2021 | Tan | C11D 3/20 |
| 2022/0112449 A1* | 4/2022 | MacNamara | C11D 17/042 |
| 2023/0008032 A1* | 1/2023 | Tan | C11D 3/3753 |

FOREIGN PATENT DOCUMENTS

| | | | | |
|---|---|---|---|---|
| CN | 1202517 | A | | 12/1998 |
| CN | 2352536 | Y | | 12/1999 |
| CN | 1250085 | A | | 4/2000 |
| CN | 1421519 | A | | 6/2003 |
| CN | 1583991 | A | | 2/2005 |
| CN | 101835459 | A | | 9/2010 |
| CN | 102492573 | A | | 6/2012 |
| CN | 202744521 | U | | 2/2013 |
| CN | 202754982 | U | | 2/2013 |
| CN | 102732392 | B | | 9/2013 |
| CN | 102965223 | B | | 1/2014 |
| CN | 103608448 | A | | 2/2014 |
| CN | 103740490 | A | | 4/2014 |
| CN | 105199887 | A | * | 12/2015 |
| CN | 105199887 | A | | 12/2015 |
| CN | 105238584 | A | | 1/2016 |
| CN | 105462733 | A | | 4/2016 |
| CN | 105586165 | A | | 5/2016 |
| CN | 105602773 | A | | 5/2016 |
| CN | 105647716 | A | | 6/2016 |
| CN | 205398584 | U | | 7/2016 |
| CN | 105861168 | A | | 8/2016 |
| CN | 105886142 | A | | 8/2016 |
| CN | 205420320 | U | | 8/2016 |
| CN | 106635572 | A | | 5/2017 |
| CN | 106715667 | A | | 5/2017 |
| CN | 111867798 | A | * | 10/2020 ........... A61K 8/0216 |
| EP | 0234867 | B1 | | 1/1993 |
| EP | 0999262 | A1 | | 5/2000 |
| JP | S638496 | A | | 1/1988 |
| JP | S6312466 | A | | 1/1988 |
| JP | S63150396 | A | | 6/1988 |
| JP | H04202600 | A | | 7/1992 |
| JP | H06308496 | A | | 11/1994 |
| JP | H06312466 | A | | 11/1994 |
| JP | H06315396 | A | | 11/1994 |
| JP | H08132454 | A | | 5/1996 |
| JP | H1072599 | A | | 3/1998 |
| JP | 2000169896 | A | | 6/2000 |
| JP | 2001089797 | A | | 4/2001 |
| JP | 2001121638 | A | | 5/2001 |
| JP | 2008122043 | A | | 5/2008 |
| JP | 4509284 | B2 | | 5/2010 |
| KR | 20080111815 | A | | 12/2008 |
| KR | 20090036882 | A | | 4/2009 |
| KR | 20090036883 | A | | 4/2009 |
| KR | 20100090122 | A | | 8/2010 |
| KR | 20100096985 | A | | 9/2010 |
| KR | 101146292 | B1 | | 5/2012 |
| KR | 20120127174 | A | | 11/2012 |
| KR | 20120130693 | A | | 12/2012 |
| RU | 2267524 | C2 | | 1/2006 |
| WO | 2009095891 | A1 | | 8/2009 |
| WO | WO-2009095891 | A1 | * | 8/2009 ........... A61K 8/0208 |
| WO | 2009129358 | A2 | | 10/2009 |
| WO | 2010077627 | A2 | | 7/2010 |
| WO | 2010077628 | A2 | | 7/2010 |
| WO | 2010135238 | A1 | | 11/2010 |
| WO | 2011014401 | A2 | | 2/2011 |
| WO | 2011014643 | A1 | | 2/2011 |
| WO | 2012138820 | A1 | | 10/2012 |
| WO | 2012157851 | A1 | | 11/2012 |
| WO | 2014059252 | A2 | | 4/2014 |
| WO | 2018140668 | A1 | | 8/2018 |
| WO | 2020072216 | A1 | | 4/2020 |
| WO | WO-2020147005 | A1 | * | 7/2020 ........... A61K 8/0208 |
| WO | WO-2022037093 | A1 | * | 2/2022 ............. A61K 45/06 |

OTHER PUBLICATIONS

Unpublished U.S. Appl. No. 17/368,884, filed on Jul. 7, 2021, to Hongsing Tan et. al.

Unpublished U.S. Appl. No. 17/368,893, filed on Jul. 7, 2021, to Hongsing Tan et. al.

All Office Actions; U.S. Appl. No. 18/504,425, filed on Nov. 8, 2023.

Unpublished U.S. Appl. No. 18/504,425, filed on Nov. 8, 2023 to Hongsing Tan et al.

* cited by examiner

MULTILAYER DISSOLVABLE SOLID ARTICLE WITH APERTURES OR HOLES

FIELD OF THE INVENTION

This invention relates to a consumer product useful for skin care, personal care, home care or laundry care, which is provided in form of a dissolvable solid article comprising two or more flexible and dissolvable sheets with one or more apertures or holes that extend therethrough.

BACKGROUND OF THE INVENTION

Personal care compositions or laundry detergent compositions in a sheet-like form that are completely dissolvable in water have become more popular. Such sheets are typically formed of a water-soluble polymer, one or more detersive surfactants, and optionally one or more other detersive actives, in which the water-soluble polymer functions as a film-former and a carrier for the detersive surfactants and other actives. Unlike the conventional liquid compositions, such sheets contain little or no water, therefore they are extremely concentrated, easy to transport and handle with little or no risk of leakage, chemically and physically stable during shipment and storage, and have a significantly smaller physical and environmental footprint.

A single sheet as mentioned hereabove can only deliver a limited amount of surfactant, and its cleaning power is therefore limited. Therefore, it may be desirable to form multilayer structures containing a plurality of such sheets stacked together, to deliver a higher dosage of surfactant for improved cleaning benefit. However, the dissolution rate of such multilayer structures may be significantly slower than a single sheet. There is also a risk that such multilayer structures may not completely dissolve under certain stringent washing conditions (e.g., cold water or extremely hard water, or low water washing conditions), and may leave undissolved residues, which can become a big consumer "pain point". Such dissolution problem may be further exacerbated if the thickness of such multilayer structures reaches a certain threshold (e.g., more than 2 mm or 3 mm).

Therefore, there is a continuing need for improving the dissolution rate of such multilayer structures (especially those with a thickness that is 2 mm or above) and reducing the risk of forming undissolved residues after wash.

SUMMARY OF THE INVENTION

The present invention employs through-apertures or through-holes of a relatively narrow size range (e.g., 0.2-0.8 mm in width or diameter) to improve the dissolution rate of the above-mentioned multilayer structures. Specifically, inventors of the present invention have discovered, surprisingly and unexpectedly, through-apertures or through-holes that are either larger or smaller in size (i.e., with widths or diameters that are either below or above the 0.2-0.8 mm range) result in slower dissolution rates.

The present invention is related, in one aspect, to a dissolvable solid article comprising two or more flexible and dissolvable sheets, wherein each of said two or more sheets comprises a water-soluble polymer; wherein said dissolvable solid article has a thickness of no less than about 2 mm; wherein said article has opposing first and second surfaces; wherein said article comprises one or more apertures or holes that extend from said first surface therethrough to said second surface; wherein each of said one or more apertures or holes is characterized by a width or diameter ranging from about 0.2 mm to about 0.8 mm, preferably from about 0.3 mm to about 0.6 mm, preferably from about 0.4 mm to about 0.5 mm.

Preferably, the sum of the volumes of said one or more apertures or holes is from 0.1% to 20%, preferably from 0.5% to 15%, more preferably from 1% to 10%, most preferably from 2% to 5%, by total volume of said article.

In one specific embodiment, such dissolvable solid article may comprise from about 4 to about 100 of said holes, wherein said holes are preferably spaced apart by equal distances. In another specific embodiment, such dissolvable solid article may comprise from about 1 to about 10 of said apertures, wherein each of said apertures has a length ranging from about 1 cm to about 20 cm, preferably from about 1.5 cm to about 10 cm, more preferably from about 2 cm to about 5 cm.

Preferably, each of said two or more flexible and dissolvable layers is characterized by a thickness ranging from about 0.1 mm to about 10 mm, preferably from about 0.2 mm to about 5 mm, more preferably from about 0.5 mm to about 2 mm, most preferably from about 0.8 mm to about 1.2 mm. The dissolvable solid article of the present invention may comprise from about 4 to about 50, preferably from about 5 to about 40, more preferably from about 6 to about 30, of said flexible and dissolvable sheets. Further, the thickness of the dissolvable solid article may range from about 3 mm to about 20 cm, preferably from about 4 mm to about 10 cm, more preferably from about 5 mm to about 30 mm.

In a particularly preferred embodiment of the present invention, at least one of said two or more flexible and dissolvable sheets may comprise from about 15% to about 40% of the water-soluble polymer by total weight of said sheet. More preferably, said at least one sheet further comprises from about 30% to about 80% of a surfactant by total weight of said sheet, and optionally one or more additional ingredients.

Further, the dissolvable solid article of the present invention may be characterized by a maximum dimension D along a direction that is perpendicular to its thickness z, wherein the ratio of D/z ranges from about 1 to about 10, preferably from about 1.4 to about 9, more preferably from about 1.5 to about 8, most preferably from about 2 to about 7.

The density of such dissolvable solid article may range from about 0.1 g/cm$^3$ to about 0.4 g/cm$^3$, preferably from about 0.15 g/cm$^3$ to about 0.25 g/cm$^3$, and it may have a final moisture content of from about 0.5% to about 25%, preferably from about 1% to about 20%, more preferably from about 3% to about 10%, by weight of said article.

These and other aspects of the present invention will become more apparent upon reading the following detailed description of the invention.

DETAILED DESCRIPTION OF THE INVENTION

Features and benefits of the various embodiments of the present invention will become apparent from the following description, which includes examples of specific embodiments intended to give a broad representation of the invention. Various modifications will be apparent to those skilled in the art from this description and from practice of the invention. The scope of the present invention is not intended to be limited to the particular forms disclosed and the invention covers all modifications, equivalents, and alternatives falling within the spirit and scope of the invention as defined by the claims.

Definitions

The term "dissolvable" as used herein refers to the ability of an article to completely or substantially dissolve in a sufficient amount of deionized water at 20° C. and under the atmospheric pressure within eight (8) hours without any stirring, leaving less than 5 wt % undissolved residues.

The term "solid" as used herein refers to the ability of an article to substantially retain its shape (i.e., without any visible change in its shape) at 20° C. and under the atmospheric pressure, when it is not confined and when no external force is applied thereto.

The term "flexible" as used herein refers to the ability of an article to withstand stress without breakage or significant fracture when it is bent at 90° along a center line perpendicular to its longitudinal direction. Preferably, such article can undergo significant elastic deformation and is characterized by a Young's Modulus of no more than 5 GPa, preferably no more than 1 GPa, more preferably no more than 0.5 GPa, most preferably no more than 0.2 GPa.

The term "sheet" as used herein refers to a non-fibrous structure having a three-dimensional shape, i.e., with a thickness, a length, and a width, while the length-to-thickness aspect ratio and the width-to-thickness aspect ratio are both at least about 5:1, and the length-to-width ratio is at least about 1:1. Preferably, the length-to-thickness aspect ratio and the width-to-thickness aspect ratio are both at least about 10:1, more preferably at least about 15:1, most preferably at least about 20:1; and the length-to-width aspect ratio is preferably at least about 1.2:1, more preferably at least about 1.5:1, most preferably at least about 1.618:1.

The term "water-soluble" as used herein refers to the ability of a sample material to completely dissolve in or disperse into water leaving no visible solids or forming no visibly separate phase, when at least about 25 grams, preferably at least about 50 grams, more preferably at least about 100 grams, most preferably at least about 150 grams, of such material is placed in one liter (1 L) of deionized water at 20° C. and under the atmospheric pressure with sufficient stirring.

The term "aperture" as used herein refers to an opening having a length (i.e., the maximum dimension) and a width (i.e., the minimal dimension that is perpendicular to said maximum dimension), while the length-to-width ratio is more than 5:1. Such opening may have a substantially linear shape (e.g., a straight slit), or it may be curved (e.g., a crescent or semi-circular slit), bent (e.g., a polygonal slit) or event serrated.

The term "hole" as used herein refers to an opening having a length (i.e., the maximum dimension) and a width (i.e., the minimal dimension that is perpendicular to said maximum dimension), while the length-to-width ratio is no more than 5:1. Such hole can have any regular or irregular shape, e.g., triangular, rectangular, square, oblong, polygonal, oval, circular, star, flower, and the like.

The term "diameter" as used in association with holes refers to the average of its length (i.e., the maximum dimension) and its width (i.e., the minimal dimension that is perpendicular to said maximum dimension).

The term "Volume Percentage" of the apertures and/or holes as used herein refers to the percentage of the total apertures/holes volume over the total volume of the dissolvable solid article, while the total apertures/holes volume is calculated as the total cross-sectional area of such openings times the thickness of the dissolvable solid article, which is calculated as follows:

$$V_{Total} = \Sigma_{i=1}^{n} (L_i \times W_i) \times T$$

wherein $V_{Total}$ is the sum of volumes of the apertures and/or holes; wherein n is the total number of apertures and/or holes; wherein $L_i$ is the length of each aperture or hole i; wherein $W_i$ is the width of each aperture or hole i; and wherein T is the thickness of the dissolvable solid article.

The term "thickness" as used herein refers to the average thickness of an article across its entire surface, preferably measured by a non-contact thickness measurement method (e.g., optical or ultrasonic measurements).

The term "final moisture content" as used herein refers to the weight percentage of moisture (including both bound water and unbound water) in an article, as measured at 20° C. under the atmospheric pressure and at a relative humidity of about 50%.

As used herein, all concentrations and ratios are on a weight basis unless otherwise specified. All temperatures herein are in degrees Celsius (° C.) unless otherwise indicated. All conditions herein are at 20° C. and under the atmospheric pressure, unless otherwise specifically stated. All polymer molecular weights are determined by weight average number molecular weight unless otherwise specifically noted.

Dissolvable Solid Article With a Multilayer Structure

The dissolvable solid article as described herein can be used to make any suitable consumer products. Non-limiting examples of product type embodiments include fabric care substrate (cleaning and/or softening), dish cleaning substrates, personal care substrates containing pharmaceutical or other skin care active, hand cleansing substrates, body cleansing substrates, shaving preparation substrates, moisturizing substrates, sunscreen substrates, skin care substrates, especially chronic skin benefit agent substrates (e.g., vitamin-containing substrates, alpha-hydroxy acid-containing substrates, etc.), hair shampoo or other hair treatment substrates, deodorizing substrates, fragrance-containing substrates, pet care substrates, and so forth.

The dissolvable solid article of the present invention is characterized by a multilayer structure, i.e., it comprises two or more flexible and dissolvable sheets as described hereinafter. Specifically, it can be made by stacking or layering two or more flexible and dissolvable sheets together to form a stack or multilayer structure first, and then slicing or cutting the resulting stack or multilayer structure into desired sizes by a slicing/cutting device downstream. Preferably, the dissolvable solid article comprises from about 4 to about 50, preferably from about 5 to about 40, more preferably from about 6 to about 30, of such flexible and dissolvable sheets that are stacked or layered together.

The thickness of the dissolvable solid article of the present invention is at least about 2 mm or above, preferable from about 3 mm to 20 cm, more preferably from about 4 mm to about 10 cm, most preferably from about 5 mm to about 30 mm. Multilayer structures of the above-described thickness present a uniquely challenging dissolution issue (in comparison with single layer structures or thinner multilayer structures), which can be effectively resolved by the present invention through specifically sized perforations (i.e., apertures or holes of specific widths or diameters).

Specifically, the multilayer dissolvable solid article of the present invention comprises one or more through-apertures or through-holes, i.e., apertures or holes that extend through the entire thickness of such article from a first surface to an opposing, second surface thereof. Each of such through-apertures or through-holes is characterized by a width (for apertures) or diameter (for holes) ranging from about 0.2 mm to about 0.8 mm, preferably from about 0.3 mm to about 0.6 mm, more preferably from about 0.4 mm to about 0.5 mm. It has been a surprising an unexpected discovery of the present invention that dissolvable articles with through-apertures or through-holes with widths or diameters either below or above such specifically defined range (i.e., 0.2-0.8 mm) lead to significant reduction in the dissolution rate of such dissolvable articles.

Preferably, the sum of the volume of such through-apertures and/or through-holes is from about 0.1% to about 20%, preferably from about 0.5% to about 15%, more preferably from about 1% to about 10%, most preferably from about 2% to about 5%, by total volume of the dissolvable solid article. On one hand, if the sum of the volume of such through-apertures and/or through-holes is below 0.1%, the dissolution rate of the dissolvable articles may still be limited; on the other hand, if the sum of the volume is above 15%, the structural integrity and performance of the dissolvable solid article may suffer.

The total number of such through-apertures or through-holes in the dissolvable solid article may be easily adjusted depending on the size of such article and the relative size of the through-apertures or through holes.

In a preferred embodiment of the present invention, the dissolvable solid article comprises equal-distance through-holes (i.e., the through-holes are spaced apart from each other by equal distances), the total number of which may range from about 4 to about 100, preferably from about 5 to about 90, more preferably from about 10 to about 80, still more preferably from about 20 to about 70, most preferably from about 30 to about 60. The through-holes can have any regular or irregular shape, e.g., triangular, rectangular, square, oblong, polygonal, oval, circular, star, flower, and the like.

In an alternative embodiment, the dissolvable solid article comprises through-apertures, the total number of which may range from 1 to about 10, preferably from about 2 to about 8, more preferably from about 4 to about 6. Each of such through-apertures may have a length ranging from about 1 cm to about 20 cm, preferably from about 1.5 cm to about 10 cm, more preferably from about 2 cm to about 5 cm. The through-apertures may have any suitable shape, e.g., a substantially linear shape (e.g., a straight slit), a curved shape (e.g., a crescent or semi-circular slit), bent (e.g., a polygonal slit), or event serrated.

In yet another embodiment of the present invention, the dissolvable solid article may contain a combination of the above-described through apertures and through-holes.

The above-described through-apertures or through-holes can be readily formed in the dissolvable solid article by well-known perforation tools and processes, including pins and needles, die and punch, laser perforation, and any combinations thereof.

The dissolvable solid article of the present invention can have any shape or size, and preferably its maximum dimension D (measured along a direction that is perpendicular to its thickness z) is no more than about 10 times of its thickness, e.g., from about 1 to about 10, more preferably from about 1.4 to about 9 times, still more preferably from about 1.5 to about 8, most preferably from about 2 to about 7, of the thickness z. In other words, the ratio of D/z is preferably from about 1 to about 10, more preferably from about 1.4 to about 9 times, still more preferably from about 1.5 to about 8, most preferably from about 2 to about 7.

The dissolvable solid article of the present invention is completely or substantially dissolvable. In other words, such article does not contain any water-insoluble substrate, unlike some conventional sheet-form consumer products.

Optionally, the dissolvable solid article is further processed by embossing, printing, coating and like steps, so as to impart it with lines, patterns, logos, or different surface properties or aesthetic/sensory feel.

Flexible and Dissolvable Sheets

The flexible and dissolvable sheets that make up the dissolvable solid article of the present invention are non-fibrous, i.e., they are free of or substantially free of fibrous elements. Such flexible and dissolvable sheets can be formed by first providing a slurry containing raw materials dissolved or dispersed in water, and then shaping the slurry into a sheet-like form. Drying is carried out either simultaneously with the shaping step, or it can be carried out subsequently, to remove water and form a finished sheet.

The flexible and dissolvable sheets of the present invention are completely or substantially dissolvable. So is the dissolvable solid article. In other words, neither the dissolvable solid article nor the flexible and dissolvable sheets contain any water-insoluble substrate, as some of the conventional laundry detergent sheets do.

The flexible and dissolvable sheets of the present invention can have any shape or size, as long as its thickness, its length, and its width are characterized by a length-to-thickness aspect ratio of at least about 5:1, a width-to-thickness aspect ratio of at least about 5:1, and a length-to-width aspect ratio of at least about 1:1. Preferably, the length-to-thickness aspect ratio and the width-to-thickness aspect ratio are both at least about 10:1, and the length-to-width aspect ratio is at least about 1.2:1. More preferably, the length-to-thickness aspect ratio and the width-to-thickness aspect ratio are both at least about 15:1, and the length-to-width aspect ratio is at least about 1.5:1. Most preferably, the length-to-thickness aspect ratio and the width-to-thickness aspect ratio are both at least about 20: 1, and the length-to-width aspect ratio is at least about 1.618:1. The thickness of the laundry detergent sheet of the present invention may range from about 0.1 mm to about 10 mm, preferably from about 0.2 mm to about 5 mm, more preferably from about 0.3 mm to about 4 mm, and most preferably from about 0.5 mm to about 2 mm. The width of each of the flexible and dissolvable sheets may range from about 2 cm to about 1 meter, preferably from about 5 cm to about 50 cm, more preferably from about 10 cm to about 40 cm. The length of each of the flexible and dissolvable sheets may range from about 2 cm to about 50 meters, preferably from about 5 cm to about 1 meter, and more preferably from about 10 cm to about 80 cm.

In a preferred but not necessary embodiment of the present invention, each of the flexible and dissolvable sheets has a golden rectangular shape (i.e., with a length-to-width aspect ratio of about 1.618:1), and it is characterized by a width of about 5-10 cm and a thickness of about 0.5 mm to about 2 mm. Such a golden rectangular shape is aesthetically pleasing and delightful to the consumers, so the resulting dissolvable solid articled formed by stacking a plurality of such flexible and dissolvable sheets together is also characterized by a similar golden rectangular shape.

Preferably, the flexible and dissolvable sheet of the present invention has certain attributes that render it aesthetically pleasing to the consumers. For example, the sheet may have a relatively smooth surface, thereby providing a pleasant feel when touched by the consumer.

It is also desirable that the flexible and dissolvable sheet of the present invention is strong enough to withstand substantive mechanical forces without losing its structural integrity, yet at the same time is sufficiently flexible for easy packaging and storage.

Water-Soluble Polymer

Each of the flexible and dissolvable sheets in the dissolvable solid article comprises one or more water-soluble polymers, which preferably function as film-formers and as carriers for active ingredients (e.g., surfactants, builders, softeners, enzymes, emollients, perfumes, colorants, bleaches, and the like). The total amount of such water-soluble polymer(s) may range, for example, from about 5% to about 90%, preferably from about 10% to about 50%, more preferably from about 15% to about 40%, most preferably from about 20% to about 30%, by total weight of such sheet.

The water-soluble polymers for use in the present invention may be either synthetic or natural in origin and may be chemically and/or physically modified.

Suitable examples of water-soluble polymers for the practice of the present invention include polyalkylene glycols (also referred to as polyalkylene oxides or polyoxyalkylenes), polyvinyl alcohols, polysaccharides (such as starch or modified starch, cellulose or modified cellulose, pullulan, xanthum gum, guar gum, and carrageenan), polyacrylates and derivatives thereof (e.g., polymethacrylates, polymethylmethacrylates, and the like), copolymers of maleic acid and (meth)acrylic acid, copolymers of methylvinyl ether and maleic anhydride, polyamines, polyethyleneimines, polyamides, polyacrylamides and derivatives thereof (e.g., polymethylacrylamides, polydimethylacrylamides, and the like), polyvinylpyrrolidones, copolymers of vinylpyrrolidone and vinyl acetate, copolymers of vinylpyrrolidone and caprolactam, polycaprolactams, polyethylene glycol monomethacrylates, polyurethanes, polycarboxylic acids, polyvinyl acetates, copolymers of vinyl acetate and crotonic acid, polyesters, proteins/polypeptides or hydrolyzed products thereof (such as collagen and gelatin), and combinations thereof.

The water-soluble polymers of the present invention may be selected from naturally sourced polymers, including those of plant origin, such as karaya gum, tragacanth gum, gum Arabic, acemannan, konjac mannan, acacia gum, gum ghatti, whey protein isolate, and soy bean isolate; seed extracts including guar gum, locust bean gum, quince seed, and psyllium seed; seaweed extracts such as Carrageenan, alginates, and agar; fruit extracts (pectins); those of microbial origin, such as xanthan gum, gellan gum, pullulan, hyaluronic acid, chondroitin sulfate, and dextran; and those of animal origins, such as casein, gelatin, keratin hydrolysates, sulfonic keratins, albumin, collagen, glutelin, glucagons, gluten, zein, and shellac.

The above-mentioned naturally sourced polymers may be modified for use in the present invention. Suitable modified natural polymers include, but are not limited to, cellulose derivatives such as methylcellulose, hydroxymethylcellulose, ethylcellulose, hydroxyethylcellulose, hydroxypropylmethylcellulose, hydroxypropylcellulose, carboxymethylcellulose, cellulose acetate phthalate, nitrocellulose and other cellulose ethers/esters; and guar derivatives such as hydroxypropyl guar.

Preferably, the water-soluble polymer to be used in the present invention is selected from the group consisting of polyalkylene glycols, polyvinyl alcohols, starch or modified starch, pullulan, gelatin, cellulose or modified cellulose (e.g., hydroxypropylmethylcellulose, methylcellulose, and carboxymethylcellulose), polyacrylates, polymethacrylates, polyacrylamides, polyvinylpyrrolidones, and combinations thereof. In a particularly preferred embodiment of the present invention, each of the flexible and dissolvable sheets contains a polyethylene glycol (PEG) or a polyvinyl alcohol (PVA), either alone (i.e., without other film formers) or in combination with starch, modified starch, cellulose, or modified cellulose.

In the execution of PEG, the PEG may be selected from poly(ethylene glycol) homopolymers and poly (ethylene glycol) copolymers having a weight average molecular weight of between about 2,000 and about 100,000 g/mol, preferably between about 4,000 and about 90,000 g/mol, and more preferably between about 6,000 and about 8,000 g/mol. Suitable poly(ethylene glycol) copolymers preferably contain at least about 50 wt % of PEG and may be selected from the group consisting of poly(lactide-block-ethylene glycol), poly(glycolide-block-ethylene glycol), poly(lactide-co-caprolactone)-block-poly(ethylene glycol), poly(ethylene glycol-co-lactic acid), poly(ethylene glycol-co-glycolic acid), poly(ethylene glycol-co-poly(lactic acid-co-glycolic acid), poly(ethylene glycol-co-propylene glycol), poly(ethylene oxide-block-propylene oxide-block-ethylene oxide), poly(propylene oxide-block-ethylene glycol-block-propylene glycol), and poly(ethylene glycol-co-caprolactone). Exemplary poly(ethylene glycol) homopolymers are commercially available from Sigma Aldrich, or from Dow under the tradename of CARBOWAX™, or from BASF under the tradename of Pluriol®. Exemplary poly(ethylene glycol) copolymers are commercially available from BASF under the tradenames of Pluronic® F127, Pluronic® F108, Pluronic® F68 and Pluronic® P105. A particularly preferred PEG for the practice of the present invention is a poly (ethylene glycol) homopolymer having a weight average molecular weight of between about 6,000 and about 80,000 g/mol.

In the execution of PVA, the PVA may be unmodified or modified, e.g., carboxylated or sulfonated. Preferably, the PVA is partially or fully alcoholised or hydrolysed. For example, it may be from 40 to 100%, preferably 70 to 92%, more preferably 88% to 92%, alcoholised or hydrolysed. The degree of hydrolysis is known to influence the temperature at which the PVA starts to dissolve in water, e.g., 88% hydrolysis corresponds to a PVA film soluble in cold (i.e. room temperature) water, whereas 92% hydrolysis corresponds to a PVA film soluble in warm water. Such PVA preferably has a weight average molecular weight ranging from about 10,000 to about 500,000 Daltons, preferably from about 15,000 to about 200,000 Daltons, more preferably from about 20,000 to about 100,000 Daltons. Further, it is preferred that the PVA has a degree of polymerization ranging from about 200 to about 12,000, preferably from about 300 to about 5,000, more preferably from about 400 to about 2000. The PVA can be selected from either a PVA homopolymer or a PVA copolymer, including copolymers of vinyl alcohol and maleic acid. An example of preferred PVA is ethyoxylated PVA. A more preferred example of PVA is commercially available from Sekisui Specialty Chemicals America, LLC (Dallas, Texas) under the tradename CEL- VOL®, including CELVOL® 523, CELVOL® 530, CELVOL® 540, CELVOL® 518, CELVOL® 513, CELVOL® 508, CELVOL® 504, and combinations thereof. Another more preferred example of PVA is the so-called G Polymer commercially available Nippon Ghosei.

In the execution of modified natural polymers, such polymers may be hydroxypropylmethylcelluloses available from Dow Chemical Company (Midland, MI) under the METHOCEL™ trade name, which include but are not limited to: METHOCEL™ E50, METHOCEL™ E15, METHOCEL™ E6, METHOCEL™ E5, METHOCEL™ E3, METHOCEL™ F50, METHOCEL™ K100, METHOCEL™ K3, METHOCEL™ A400, and combinations thereof.

The water-soluble polymer may be present in the flexible and dissolvable sheets of the present invention at from about 1% to about 70%, preferably from about 2% to about 60%, more preferably from about 5% to about 50%, and most preferably from about 15% to about 40%, by total weight of each sheet.

In addition to the water-soluble polymer(s), each of the flexible and dissolvable sheets may also comprise suitable additives such as plasticizers and solids, for modifying the properties of the water-soluble polymer(s).

Suitable plasticizers can be selected from the group consisting of polyols, copolyols, polycarboxylic acids, polyesters, and dimethicone copolyols. For example, pentaerythritols (such as depentaerythritol), sugar alcohols (such as sorbitol and mannitol), glycols (such as glycerol, ethylene glycol, and propylene glycol) and polyethylene glycols with molecular weight ranging from about 200 to about 600 can be readily used as plasticizers in the flexible and dissolvable sheets of the present invention. Most preferred plasticizers include glycerol and propylene glycol. Plasticizers are generally used in an amount of up to 35 wt %, for example from 1 to 35 wt %, preferably from 3 to 20 wt %, more preferably from 5 to 15 wt % by total weight of each sheet.

Solids such as talc, stearic acid, magnesium stearate, silicon dioxide, zinc stearate or colloidal silica may also be used, generally in an amount ranging from about 0.5 to 5 wt % by total weight of each sheet.

Active Ingredients

Each of the flexible and dissolvable sheets of the present invention further contains one or more active ingredients with certain functional benefits, in addition to the water-soluble polymer(s) discussed hereinabove.

Surfactants

Preferably, at least one of the flexible and dissolvable sheets of the present invention contains one or more detersive surfactants selected from the group consisting of anionic surfactants, nonionic surfactants, cationic surfactants, amphoteric surfactants, zwitterionic surfactants, and combinations thereof. More preferably, all of the flexible and dissolvable sheets in the dissolvable solid article contain one or more surfactants as listed hereinabove.

Preferably, at least one of the flexible and dissolvable sheets comprises from about 15% to about 90%, preferably from about 20% to about 85%, more preferably from about 30% to about 80%, most preferably from about 40% to about 70%, of surfactant(s) by total weight of said sheet. It is particularly preferred that at least one of said flexible and dissolvable sheets is characterized by a sufficiently high surfactant content, e.g., at least 30%, preferably at least 50%, more preferably at least 60%, and most preferably at least 70% by total weight of such sheet. Such a high surfactant content provides a very compact and concentrated detergent product, which is particularly convenient for consumers who travel often. Further, shipping and handling costs for such compact and concentrated form are significantly reduced, in comparison with the traditional powder or liquid forms of detergent products, which make the detergent product formed according to the present invention particularly desirable to be marketed through e-commerce channels.

Non-limiting examples of anionic surfactants suitable for use in the present invention include alkyl sulfates, alkyl ether sulfates, sulfated monoglycerides, sulfonated olefins, alkyl aryl sulfonates, primary or secondary alkane sulfonates, alkyl sulfosuccinates, acyl taurates, acyl isethionates, alkyl glyceryl ether sulfonate, sulfonated methyl esters, sulfonated fatty acids, alkyl phosphate, acyl glutamates, acyl sarcosinates, alkyl sulfoacetates, acylated peptides, alkyl ether carboxylates, acyl lactylates, anionic fluorosurfactants, sodium lauroyl glutamate, and combinations thereof.

Preferably, one or more anionic surfactant(s) as mentioned hereinabove is functioning as the main surfactant in at least one of the flexible and dissolvable sheets, i.e., being present at an amount of about 50% or more, by total weight of all surfactants in such sheet. Suitable anioni surfactants for use as the main surfactant in the present invention include unalkoxylated $C_6$-$C_{20}$ linear or branched alkyl sulfates (AS), $C_6$-$C_{20}$ linear alkylbenzene sulfonates (LAS), alkoxylated $C_6$-$C_{20}$ linear or branched alkyl sulfates (AAS), and combinations thereof.

A particularly preferred type of surfactants for use as the main surfactant in the flexible and dissolvable sheets of the present invention are unalkoxylated $C_6$-$C_{18}$ AS, which are referred to as "mid-cut AS" hereinafter, while each of which has a branched or linear unalkoxylated alkyl group containing from about 6 to about 18 carbon atoms. In a particularly preferred embodiment of the present invention, the mid-cut AS is present as the main surfactant in the flexible and dissolvable sheet, i.e., it is present in an amount that is at least about 50% by total weight of all surfactants in the sheet, while another surfactant, such as LAS, AAS, and/or nonionic surfactant, is present as a co-surfactant.

The mid-cut AS of the present invention has the generic formula of R—O—$SO_3^-M^+$, while R is branched or linear unalkoxylated $C_6$-$C_{18}$ alkyl group, and M is a cation of alkali metal, alkaline earth metal or ammonium. Preferably, the R group of the AS surfactant contains from about 8 to about 16 carbon atoms, more preferably from about 10 to about 14 carbon atoms, and most preferably from about 12 to about 14 carbon atoms. R can be substituted or unsubstituted, and is preferably unsubstituted. R is substantially free of any alkoxylation. M is preferably a cationic of sodium, potassium, or magnesium, and more preferably M is a sodium cation.

The amount of mid-cut AS surfactants used in the present invention may range from about 5% to about 90%, preferably from about 10% to about 80%, more preferably from about 20% to about 75%, and most preferably from about 30% to about 70%, by total weight of each of such two or more non-fibrous sheets. Such mid-cut AS surfactant(s) preferably functions as the main surfactant in the surfactant system of the flexible and dissolvable sheets. In other words, the mid-cut AS surfactant(s) are present in an amount of greater than 50% by total weight of all surfactants in each of the flexible and dissolvable sheets.

Preferably, the surfactant system of the sheets may contain a mixture of mid-cut AS surfactants comprising more than about 50 wt %, preferably more than about 60 wt %, more preferably more than 70 wt % or 80 wt %, and most preferably more than 90 wt % or even at 100 wt % (i.e., substantially pure), of linear AS surfactants having an even number of carbon atoms, including, for example, $C_6$, $C_8$, $C_{10}$, $C_{12}$, $C_{14}$, $C_{16}$, and $C_{18}$ AS surfactants.

More preferably, the surfactant system of the sheets contains a mixture of mid-cut AS surfactants, in which $C_6$-$C_{14}$ AS surfactants are present in an amount ranging from about 85% to about 100% by total weight of the mixture. This mixture can be referred to as a "$C_6$-$C_{14}$-rich AS mixture." More preferably, such $C_6$-$C_{14}$-rich AS mixture contains from about 90 wt % to about 100 wt %, or from 92 wt % to about 98 wt %, or from about 94 wt % to about 96 wt %, or 100 wt % (i.e., pure), of $C_6$-$C_{14}$ AS.

In a particularly preferred embodiment of the present invention, the surfactant system contains a mixture of mid-cut AS surfactants comprising from about 30 wt % to about 100 wt % or from about 50 wt % to about 99 wt %, preferably from about 60 wt % to about 95 wt %, more preferably from about 65 wt % to about 90 wt %, and most preferably from about 70 wt % to about 80 wt % of $C_{12}$-$C_{14}$ AS, which can be referred to as a "$C_{12}$-$C_{14}$-rich AS mixture." Preferably, such $C_{12}$-$C_{14}$-rich AS mixture contains a majority of $C_{12}$ AS. In a most preferred embodiment of the present invention, the surfactant system contains a mixture of mid-cut AS surfactants that consist of $C_{12}$ and/or $C_{14}$ AS surfactants, e.g., 100% $C_{12}$ AS or from about 70 wt % to about 80 wt % of $C_{12}$ AS and from 20 wt % to about 30 wt % of $C_{14}$ AS, with little or no other AS surfactants therein.

In a most preferred embodiment of the present invention, each of the flexible and dissolvable sheets contains from about 10 wt % to about 70 wt %, preferably from about 20 wt % to about 60 wt %, of pure $C_{12}$ AS or a $C_{12}$-$C_{14}$-rich AS mixture by total weight of such sheet, while the $C_{12}$-$C_{14}$-rich AS mixture contains from about 70 wt % to about 80 wt % of $C_{12}$ AS and from 20 wt % to about 30 wt % of $C_{14}$ AS by total weight of such mixture.

A commercially available mid-cut AS mixture particularly suitable for practice of the present invention is Texapon® V95 G from Cognis (Monheim, Germany).

Another preferred type of surfactants for use as the main surfactant in the flexible and dissolvable sheets of the present invention are $C_6$-$C_{20}$ linear alkylbenzene sulfonates (LAS), which may be present in the sheets either alone or in combination with the mid-cut AS described hereinabove. LAS can either be present as a main surfactant, or as a co-surfactant for the mid-cut AS, in the sheets. In a particularly preferred embodiment of the present invention, LAS is present in the flexible and dissolvable sheets as a co-surfactant for the mid-cut AS, for example, in a weight ratio ranging from about 1:15 to about 1:2, preferably from about 1:10 to about 1:3, and more preferably from about 1:8 to about 1:4.

LAS surfactants are well known in the art and can be readily obtained by sulfonating commercially available linear alkylbenzenes. Exemplary $C_6$-$C_{20}$ linear alkylbenzene sulfonates that can be used in the present invention include alkali metal, alkaline earth metal or ammonium salts of $C_6$-$C_{20}$ linear alkylbenzene sulfonic acids, and preferably the sodium, potassium, magnesium and/or ammonium salts of $C_{11}$-$C_{18}$ or $C_{11}$-$C_{14}$ linear alkylbenzene sulfonicacids. More preferred are the sodium or potassium salts of $C_{12}$ linear alkylbenzene sulfonic acids, and most preferred is the sodium salt of $C_{12}$ linear alkylbenzene sulfonic acid, i.e., sodium dodecylbenzene sulfonate. If present, the amount of LAS in the flexible and dissolvable sheets may range from about 1% to about 90%, preferably from about 2% to about 70%, and more preferably from about 5% to about 40%, by total weight of each of the sheets. In a most preferred embodiment of the present invention, each of the sheets contains from about 5% to about 20% of a sodium, potassium, or magnesium salt of $C_{12}$ linear alkylbenzene sulfonic acid, by total weight of such sheet.

The flexible and dissolvable sheet of the present invention may contain, either alone as a main surfactant, or preferably in combination with the mid-cut AS and/or LAS described hereinabove as a co-surfactant, a $C_6$-$C_{20}$ linear or branched alkylalkoxy sulfate (AAS) having an average degree of alkoxylation ranging from about 0.1 to about 5.

The AAS surfactants preferably are $C_6$-$C_{20}$ linear or branched alkylethoxy sulfate (AES) with the following formula (I):

$$R\text{—}O\text{—}(C_2H_4O)_x\text{—}SO_3^-M^+ \qquad (I),$$

wherein R is a linear or branched alkyl chain having from 10 to 20 carbon atoms, either saturated or unsaturated; x averages from 1 to 3; and M is selected from the group consisting of alkali metal ions, ammonium, or substituted ammonium. Preferably, R is a linear or branched alkyl chain having from 12 to 16 carbon atoms; x averages 3; and M is sodium. The most preferred anionic surfactant for the practice of the present invention is sodium lauryl ether sulphate with an average degree of ethoxylation of about 3.

The AAS surfactants, if present, can be provided in an amount ranging from about 1% to about 30%, preferably from about 2% to about 20%, more preferably from about 5% to about 15%, by total weight of the flexible and dissolvable sheet.

Other anionic surfactants suitable for inclusion into the flexible and dissolvable sheets of the present invention include $C_6$-$C_{20}$ linear or branched alkyl sulfonates, $C_6$-$C_{20}$ linear or branched alkyl carboxylates, $C_6$-$C_{20}$ linear or branched alkyl phosphates, $C_6$-$C_{20}$ linear or branched alkyl phosphonates, $C_6$-$C_{20}$ alkyl N-methyl glucose amides, $C_6$-$C_{20}$ methyl ester sulfonates (MES), and combinations thereof.

More specific examples of anionic surfactants for use in the flexible and dissolvable sheets of the present invention include ammoniumlauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, and combinations thereof.

The flexible and dissolvable sheet of the present invention may contain one or more nonionic surfactants, which are to be used in combination with the anionic surfactants described hereinabove. Such nonionic surfactant(s) may be present in an amount ranging from 1% to 40%, preferably from 2% to 30%, more preferably from 5% to 25%, and most preferably from 10% to 20%, by total weight of such sheet.

Suitable nonionic surfactants useful herein can comprise any conventional nonionic surfactant. These can include, for e.g., amine oxide surfactants and alkoxylatedfatty alcohols. The nonionic surfactants may be selected from the ethoxylated alcohols and ethoxylated alkyl phenols of the formula $R(OC_2H_4)_nOH$, wherein R is selected from the group consisting of aliphatic hydrocarbon radicals containing from about 8 to about 15 carbon atoms and alkyl phenyl radicals in which the alkyl groups contain from about 8 to about 12 carbon atoms, and the average value of n is from about 5 to about 15. In one example, the nonionic surfactant is selected from ethoxylated alcohols having an average of about 24 carbon atoms in the alcohol and an average degree of ethoxylation of about 9 moles of ethylene oxide per mole of alcohol. Other non-limiting examples of nonionic surfactants useful herein include: $C_8$-$C_{18}$ alkyl ethoxylates, such as, NEODOL® nonionic surfactants from Shell; $C_6$-$C_{12}$ alkyl phenol alkoxylates where the alkoxylate units may be ethyleneoxy units, propyleneoxy units, or a mixture thereof; $C_{12}$-$C_{18}$ alcohol and $C_6$-$C_{12}$ alkyl phenol condensates with ethylene oxide/propylene oxide block polymers such as Pluronic® from BASF; $C_{14}$-$C_{22}$ mid-chain branched alcohols; $C_{14}$-$C_{22}$ mid-chain branched alkyl alkoxylates, BAE, wherein x is from 1 to 30; alkylpolysaccharides, and specifically alkylpoly glycosides; polyhydroxy fatty acid amides; and ether capped poly(oxyalkylated) alcohol surfactants. Suitable nonionic surfactants also include those sold under the tradename Lutensol® from BASF.

Preferred nonionic surfactants of the present invention include alkyl polyglucoside, alkyl alcohols, alkyl alkoxylated alcohols, alkyl alkoxylates, alkyl phenol alkoxylates, alkylcelluloses, polyhydroxy fatty acid amides, ether capped poly(oxyalkylated) alcohol surfactants. In a more preferred embodiment, the nonionic surfactant is selected from alkyl alkoxylated alcohols, such as a $C_{8-18}$ alkyl alkoxylated alcohol, and more specifically a $C_{8-18}$ alkyl ethoxylated alcohol. The alkyl alkoxylated alcohol may have an average degree of alkoxylation of from about 1 to about 50, or from about 1 to about 30, or from about 1 to about 20, or from about 1 to about 10. The alkyl alkoxylated alcohol can be linear or branched, substituted or unsubstituted.

In a most preferred embodiment, the flexible and dissolvable sheet of the present invention contains a $C_{12-14}$ alkyl ethoxylated alcohol having an average degree of ethoxylation of from about 1 to about 10, or from about 1 to about 8, or from about 3 to about 7, in an amount ranging from about 1% to about 40%, preferably from about 5% to about 25%, and more preferably from about 10% to about 20%, by total weight of the sheet.

The flexible and dissolvable sheets of the present invention may each comprise at least one additional surfactant selected from the group consisting of zwitterionic surfactants, amphoteric surfactants, cationic surfactants, and combinations thereof.

Non-limiting examples of cationic surfactants include: the quaternary ammonium surfactants, which can have up to 26 carbon atoms include: alkoxylate quaternary ammonium (AQA) surfactants; dimethyl hydroxyethyl quaternary ammonium; dimethyl hydroxyethyl lauryl ammonium chloride; polyamine cationic surfactants; cationic ester surfactants; and amino surfactants, e.g., amido propyldimethyl amine (APA). Suitable cationic detersive surfactants also include alkyl pyridinium compounds, alkyl quaternary ammonium compounds, alkyl quaternary phosphonium compounds, alkyl ternary sulphonium compounds, and mixtures thereof.

Suitable cationic detersive surfactants are quaternary ammonium compounds having the general formula:

$$(R)(R_1)(R_2)(R_3)N^+X^- \quad (II)$$

wherein, R is a linear or branched, substituted or unsubstituted $C_{6-18}$ alkyl or alkenyl moiety, $R_1$ and $R_2$ are independently selected from methyl or ethyl moieties, $R_3$ is a hydroxyl, hydroxymethyl or a hydroxyethyl moiety, X is an anion which provides charge neutrality, suitable anionsinclude: halides, for example chloride; sulphate; and sulphonate. Suitable cationic detersive surfactants are mono-$C_{6-18}$ alkyl mono-hydroxyethyl di-methyl quaternary ammonium chlorides. Highly suitable cationic detersive surfactants are mono-$C_{8-10}$ alkyl mono-hydroxyethyl di-methyl quaternary ammonium chloride, mono-$C_{10-12}$ alkyl mono-hydroxyethyl di-methyl quaternary ammonium chloride and mono-$C_{10}$ alkyl mono-hydroxyethyl di-methyl quaternary ammonium chloride.

Suitable examples of zwitterionic surfactants include: derivatives of secondary and tertiary amines, including derivatives of heterocyclic secondary and tertiary amines; derivatives of quaternary ammonium, quaternary phosphonium or tertiary sulfonium compounds; betaines, including alkyl dimethyl betaine, cocodimethyl amidopropyl betaine, and sulfo and hydroxy betaines; $C_8$ to $C_{18}$ (preferably from $C_{12}$ to $C_{18}$) amine oxides; N-alkyl-N,N-dimethylammino-1-propane sulfonate, where the alkyl group can be $C_8$ to $C_{18}$.

Suitable amphoteric surfactants include aliphatic derivatives of secondary or tertiary amines, or aliphatic derivatives of heterocyclic secondary and tertiary amines in which the aliphatic radical may be straight or branched-chain and where one of the aliphatic substituents contains at least about 8 carbon atoms, or from about 8 to about 18 carbon atoms, and at least one of the aliphatic substituents contains an anionic water-solubilizing group, e.g. carboxy, sulfonate, sulfate. Suitable amphoteric surfactants also include sarcosinates, glycinates, taurinates, and mixtures thereof.

In a particularly preferred but not necessary embodiment of the present invention, the flexible and dissolvable sheet may have a surfactant system containing only anionic surfactants, e.g., either a single anionic surfactant or a combination of two or more different anionic surfactants. Alternatively, such sheets may include a composite surfactant system, e.g., containing a combination of one or more anionic surfactants with one or more nonionic surfactants, or a combination of one or more anionic surfactants with one or more zwitterionic surfactants, or a combination of one or more anionic surfactants with one or more amphoteric surfactants, or a combination of one or more anionic surfactants with one or more cationic surfactants, or a combination of all the above-mentioned types of surfactants (i.e., anionic, nonionic, amphoteric and cationic).

Additional Ingredients

The flexible and dissolvable sheets of the present invention may optionally include one or more other adjunct detergent ingredients for assisting or enhancing cleaning performance or to modify the aesthetics of the sheet. Illustrative examples of such adjunct detergent ingredients include: (1) inorganic and/or organic builders, such as carbonates (including bicarbonates and sesquicarbonates), sulphates, phosphates (exemplified by the tripolyphosphates, pyrophosphates, and glassy polymeric meta-phosphates), phosphonates, phytic acid, silicates, zeolite, citrates, polycarboxylates and salts thereof (such as mellitic acid, succinic acid, oxydisuccinic acid, polymaleic acid, benzene 1,3,5-tricarboxylic acid, carboxymethyloxysuccinic acid, and soluble salts thereof), ether hydroxypolycarboxylates, copolymers of maleic anhydride with ethylene or vinyl methyl ether, 1,3,5-trihydroxy benzene-2,4,6-trisulphonic acid, 3,3-dicarboxy-4-oxa-1,6-hexanedioates, polyacetic acids (such as ethylenediamine tetraacetic acid and nitrilotriacetic acid) and salts thereof, fatty acids (such as $C_{12}$-$C_{18}$ monocarboxylic acids); (2) chelating agents, such as iron and/or manganese-chelating agents selected from the group consisting of amino carboxylates, amino phosphonates, polyfunctionally-substituted aromatic chelating agents and mixtures therein; (3) clay soil removal/anti-redeposition agents, such as water-soluble ethoxylated amines (particularly ethoxylated tetraethylene-pentamine); (4) polymeric dispersing agents, such as polymeric polycarboxylates and polyethylene glycols, acrylic/maleic-based copolymers and water-soluble salts thereof of, hydroxypropylacrylate, maleic/acrylic/vinyl alcohol terpolymers, polyethylene glycol (PEG), polyaspartates and polyglutamates; (5) optical brighteners, which include but are not limited to derivatives of stilbene, pyrazoline, coumarin, carboxylic acid, methinecyanines, dibenzothiphene-5,5-dioxide, azoles, 5- and 6-membered-ring heterocycles, and the like; (6) suds suppressors, such as monocarboxylic fatty acids and soluble salts thereof, high molecular weight hydrocarbons (e.g., paraffins, haloparaffins, fatty acid esters, fatty acid esters of monovalent alcohols, aliphatic $C_{18}$-$C_{40}$ ketones, etc.), N-alkylated amino triazines, propyleneoxide, monostearyl phosphates, silicones or derivatives thereof, secondary alcohols (e.g., 2-alkyl alkanols) and mixtures of such alcohols with silicone oils; (7) suds boosters, such as $C_{10}$-$C_{16}$ alkanolamides, $C_{10}$-$C_{14}$ monoethanol and diethanol amides, high sudsing surfactants (e.g., amine oxides, betaines and sultaines), and soluble magnesium salts (e.g., $MgCl_2$, $MgSO_4$, and the like); (8) fabric softeners, such as smectite clays, amine softeners and cationic softeners; (9) dye transfer inhibiting agents, such as polyvinyl pyrrolidone polymers, polyamine N-oxide polymers, copolymers of N-vinylpyrrolidone and N-vinylimidazole, manganese phthalocyanine, peroxidases, and mixtures thereof; (10) enzymes, such as proteases, amylases, lipases, cellulases, and peroxidases, and mixtures thereof; (11) enzyme stabilizers, which include water-soluble sources of calcium and/or magnesium ions, boric acid or borates (such as boric oxide, borax and other alkali metal borates); (12) bleaching agents, such as percarbonates (e.g., sodium carbonate peroxyhydrate, sodium pyrophosphate peroxyhydrate, urea peroxyhydrate, and sodium peroxide), persulfates, perborates, magnesium monoperoxyphthalate hexahydrate, the magnesium salt of metachloro perbenzoic acid, 4-nonylamino-4-oxoperoxybutyric acid and diperoxydodecanedioic acid, 6-nonylamino-6-oxoperoxycaproic acid, and photoactivated bleaching agents (e.g., sulfonated zinc and/or aluminum phthalocyanines); (13) bleach activators, such as nonanoyloxybenzene sulfonate (NOBS), tetraacetyl ethylene diamine (TAED), amido-derived bleach activators including (6-octanamidocaproyl)oxybenzenesulfonate, (6-nonanamidocaproyl)oxybenzenesulfonate, (6-decanamidocaproyl)oxybenzenesulfonate, and mixtures thereof, benzoxazin-type activators, acyl lactam activators (especially acyl caprolactams and acyl valerolactams); and (14) any other known detergent adjunct ingredients, including but not limited to carriers, hydrotropes, processing aids, dyes or pigments, and solid fillers.

Alternatively (or in addition), the flexible and dissolvable sheets of the present invention may comprise optional ingredients approved for use in cosmetics. Further non-limiting examples of such optional ingredients include preservatives, perfumes or fragrances, coloring agents or dyes, conditioning agents, hair bleaching agents, thickeners, moisturizers, emollients, pharmaceutical actives, vitamins or nutrients, sunscreens, deodorants, sensates, plant extracts, nutrients, astringents, cosmetic particles, absorbent particles, adhesive particles, hair fixatives, fibers, reactive agents, skin lightening agents, skin tanning agents, anti-dandruff agents, perfumes, exfoliating agents, acids, bases, humectants, enzymes, suspending agents, pH modifiers, hair colorants, hair perming agents, pigment particles, anti-acne agents, anti-microbial agents, sunscreens, tanning agents, exfoliation particles, hair growth or restorer agents, insect repellents, shaving lotion agents, co-solvents or other additional solvents, and similar other materials. Specifically, suitable conditioning agents include high melting point fatty compounds, silicone conditioning agents and cationic conditioning polymers.

Method of Making the Flexible and Dissolvable Sheets

The flexible and dissolvable sheets of the present invention can be made by any suitable film-forming method, such as casting, molding, pressing, extrusion/extrusion-coating, calendar rolling, solution deposition, skiving, and lamination. For example, it can be formed by first providing a slurry containing raw materials dissolved or dispersed in water, and then shaping the slurry into a sheet-like form. Drying is carried out either simultaneously with the shaping step, or it can be carried out subsequently, to remove water and form a finished sheet.

A preferred but non-limiting process for making the flexible and dissolvable sheet of the present invention by using a cylinder sheet production system is described hereinafter.

The cylinder sheet production system comprises a base bracket with a heated rotatable cylinder installed thereon. The heated rotatable cylinder can be driven by a motorized drive installed on the base bracket, and work at a predetermined rotation speed. Said heated rotatable cylinder is preferably coated with a non-stick coating on its outer surface.

There is also provided a feeding mechanism on the base bracket, which is for adding a pre-formed slurry containing all or some raw materials described hereinabove (e.g., the water-soluble polymer(s), the plasticizers, the solids, the active ingredients such as surfactant(s) and adjunct detergent and/or cosmetic ingredients) onto the heated rotatable cylinder. The feeding mechanism includes a feeding rack installed on the base bracket, while said feeding rack has installed thereupon at least one (preferably two) feeding hopper(s), an imaging device for dynamic observation of the feeding, and an adjustment device for adjusting the position and inclination angle of the feeding hopper.

There is also a heating shield installed on the base bracket, to prevent rapid heat lost. Otherwise, the slurry can solidify too quickly on the heated rotatable cylinder. The heating shield can also effectively save energy needed by the heated rotatable cylinder, thereby achieving reduced energy consumption and provide cost savings. The heating shield is a modular assembly structure, or integrated structure, and can be freely detached from the base bracket. A suction device is also installed on the heating shield for sucking the hot steam, to avoid any water condensate falling on the sheet that is being formed. There is also a start feeding mechanism installed on the base bracket, which is for scooping up the sheet already formed by the heated rotatable cylinder.

The making process of the flexible and dissolvable sheet is as follows. Firstly, the heated rotatable cylinder with the non-stick coating on the base bracket is driven by the motorized drive. Next, the adjustment device adjusts the feeding mechanism so that the distance between the feeding hopper and the outer surface of the heated rotatable cylinder reaches a preset value. Meanwhile, the feeding hopper adds the pre-formed slurry containing all or some raw materials for making the flexible and dissolvable sheet onto the heated rotatable cylinder. The suction device of the heating shield sucks the hot steam generated by the heated rotatable cylinder.

Next, the start feeding mechanism scoops up the dried sheet. The already formed flexible and dissolvable sheet can then be formed into the dissolvable solid article of the present invention, as described hereinabove.

EXAMPLES

Example 1: Comparative Test Showing Impact of Through-Hole Diameter and Volume Percentage of Through-Holes on Dissolution Rate of Dissolvable Solid Articles Flexible and dissolvable sheets having a thickness of about 1 mm and comprising the following ingredients are first made following the making process as described hereinabove.

TABLE 1

| Ingredient | wt % |
| --- | --- |
| Polyvinyl alcohol[1] | 16.6 |
| Polyvinyl alcohol[2] | 8.3 |
| $C_{12}$-$C_{14}$ alkyl sulfate | 46.4 |
| $C_{12}$-$C_{14}$ alkyl ethoxylated sulfate[3] | 18.8 |
| Glycerin | 4.2 |
| Misc. & Moisture | Balance |

[1]Degree of polymerization = 500; Mw = 22,000
[2]Degree of polymerization 1700; Mw = 74,800
[3]Having an average ethoxylation degree of about 1

Five (5) layers of the above-described 1 mm-thick flexible and dissolvable sheets are then stacked together, heat sealed, and cut to form dissolvable solid articles, each of which having a square shape of about 6 cm×6 cm and a thickness of about 5 mm.

A Hyrel System 30M 3D printer with spindle attachment is then utilized to perforate such dissolvable solid articles to form various numbers of circular-shaped through-holes of different sizes therein. The printer is capable of rotating a drill head at high speed (>1000 RPM) and precisely moving the drill head to defined X, Y and Z locations according to a customized G-code. The location of each through-hole in the respective dissolvable solid article is calculated and arrange so that the spacing between adjacent through-holes is equal, and the total number of through-holes formed in the respective dissolvable solid article is calculated based on the desired size of such through-holes and the desired Volume Percentage of all such through-holes. The following perforated dissolvable solid articles with different numbers of circular-shaped through-holes of different sizes are formed correspondingly:

TABLE II

| Article | Hole Diameter (mm) | Volume Percentage (%) of Holes | # of Holes |
| --- | --- | --- | --- |
| A | 0.1 | 1 | 4586 |
| B | 0.4 | 1 | 286 |
| C | 1 | 1 | 46 |
| D | 0.1 | 10 | 45860 |
| E | 0.4 | 10 | 2866 |
| F | 1 | 10 | 458 |

Specifically, perforation of the above-mentioned dissolvable solid articles is carried out as follows:

Each article is placed with one side touching the printer tray and the other side facing upwards. In this way the Z dimension according to the printer software corresponds to the thickness of the article.

The article is placed at a pre-determined location on the tray such that one edge of the article corresponded to the (X, Y) location of (0,0) in the G-codefile instructions.

The drill head having the required diameter is inserted into the spindle tool.

The G-code file is loaded and carried out by the software.

During the drilling process, the drill head is moved to the required X and Y locations and the drill moves up and down along the Z axis such that the holes are drilled through the entire thickness of the article.

The resulting dissolvable solid articles A-F are then subjected to dissolution tests by performing the following steps:

Four (4) samples of each of the above-mentioned dissolvable solid articles A-F are first weighted (with a combined weight of approximately 4.0 g), and the total weight is recorded as the "Total Weight of Sample Material";

Each sample is then inserted into a black cotton pouch having dimensions of approximately 8 cm×8 cm, which consists of two (2) layers of 100% cotton fabric with three sides already sealed by stitching and the fourth side left open for inserting the article;

Once the article is inserted, the black cotton pouch is then sealed by punching three (3) staples through the two layers;

The four (4) black cotton pouches, each containing a sample therein, are then added into an Electrolux W565H programmable front-loading washing machine, together with two (2) kilograms of 100% cotton terry towels, each of which has a square shape of approximately 20 cm×20 cm;

The black cotton pouch and the cotton terry towels undergo one wash cycle as described hereinafter, with a predetermined total washing time of 3 minutes:

1 Add 20 kg of reverse osmosis purified water, and the water temperature is maintained at 20° C. throughout the wash cycle
2 Accelerate the drum to 45 revolutions per minute in the clockwise direction over 2 seconds with a linear rate of acceleration
3 Maintain the drum rotation speed at 45 revolutions per minute for 22 seconds
4 Decelerate the drum to 0 revolutions per minute over 2 seconds with a linear rate of deceleration
5 Drum remains stationary for 4 seconds
6 Repeat steps 2-5 but with drum rotating in the counter-clock direction
7 Repeat steps 2-6 until the respective total washing time is reached At the end of each wash cycle, the black cotton pouches are taken out of the washing machine and opened, while any undissolved residue of the sample articles is removed from the black cotton pouches by using a laboratory spatula and then transferred to a plastic pot;

The undissolved residue is inserted into an oven preheated to 100 C and left to dry for 1 hour;

The dried residue is then weighted, and the weight is recorded as the "Weight of Undissolved Solids";

The Percentage (%) Dissolved of the sample material can then be calculated as:

$$\frac{\text{Total Weight of Sample Material} - \text{Weight of Undissolved Solids}}{\text{Total Weight of Sample Material}} \times 100\%$$

wherein the higher the Percentage (%) Dissolved, the better the dissolution rate.

The above steps are repeated for each type of dissolvable solid articles A-F, and following are the corresponding dissolution results:

TABLE III

| Article | Hole Diameter (mm) | Volume Percentage (%) of Holes | Percentage (%) Dissolved |
|---|---|---|---|
| A | 0.1 | 1 | 62.0 |
| B | 0.4 | 1 | 75.5 |
| C | 1 | 1 | 68.0 |
| D | 0.1 | 10 | 62.3 |
| E | 0.4 | 10 | 85.7 |
| F | 1 | 10 | 68.8 |

The above data shows that surprisingly and unexpectedly, dissolvable solid articles B and E with through-holes of about 0.4 mm in diameter have better dissolution rates than articles A, C, D and F with either larger or smaller through-holes of about 0.1 mm or about 1 mm in diameter.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any crossreferenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A dissolvable solid article comprising two or more flexible and dissolvable sheets, wherein each of said two or more sheets comprises a water-soluble polymer; wherein said dissolvable solid article has a thickness of no less than 2 mm; wherein said article has opposing first and second surfaces; wherein said article comprises one or more apertures or holes that extend from said first surface through said second surface; wherein each of said one or more apertures or holes is characterized by a width or diameter ranging from 0.2 mm to 0.8 mm and the sum of the volume of said one or more apertures or holes is from 0.5% to 15% by total volume of said article.

2. The dissolvable solid article of claim 1, wherein the width or diameter of each of said one or more apertures or holes ranges from 0.3 mm to 0.6 mm.

3. The dissolvable solid article according to claim 1, comprising from 4 to 100 of said holes, wherein said holes are spaced apart by equal distances.

4. The dissolvable solid article according to claim 1, comprising from 1 to 10 of said apertures, wherein each of said apertures has a length ranging from 1 cm to 20 cm.

5. The dissolvable solid article according to claim 1, wherein each of said two or more flexible and dissolvable layers is characterized by a thickness ranging from 0.1 mm to 10 mm.

6. The dissolvable solid article according to claim 1, wherein said article comprises from 4 to 50, of said flexible and dissolvable sheets.

7. The dissolvable solid article according to claim 1, wherein the thickness of said article is from 3 mm to 20 cm.

8. The dissolvable solid article according to claim 1, wherein at least one of said two or more flexible and dissolvable sheets comprises from 15% to 40% of said water-soluble polymer by total weight of said sheet.

9. The dissolvable solid article according to claim 8, wherein said at least one sheet further comprises from 30% to 80% of a surfactant by total weight of said sheet.

10. The dissolvable solid article according to claim 1, which is characterized by a maximum dimension D along a direction that is perpendicular to its thickness z, wherein the ratio of D/z ranges from 2 to 7.

11. The dissolvable solid article according to claim 1, wherein said article is characterized by a density ranging from 0.1 g/cm$^3$ to 0.4 g/cm$^3$.

12. The dissolvable solid article according to claim 1, wherein said article is characterized by a final moisture content of by weight of said article.

13. The dissolvable solid article of claim 1, wherein the Volume Percentage of said one or more apertures or holes is from 1% to 10%, by total volume of said article.

14. The dissolvable solid article of claim 1, wherein the Volume Percentage of said one or more apertures or holes is from 2% to 5%, by total volume of said article.

15. The dissolvable solid article of claim 1, wherein the width or diameter of each of said one or more apertures or holes ranges from 0.4 mm to 0.5 mm.

16. The dissolvable solid article according to claim 1, comprising from 1 to 10 of said apertures, wherein each of said apertures has a length ranging from 1.5 cm to 10 cm.

17. The dissolvable solid article according to claim 1, comprising from 1 to 10 of said apertures, wherein each of said apertures has a length ranging from 2 cm to 5 cm.

18. The dissolvable solid article according to claim 1, wherein the thickness of said article is from 4 mm to 10 cm.

19. The dissolvable solid article according to claim 1, wherein the thickness of said article is from 5 mm to 30 mm.

20. The dissolvable solid article according to claim 1, wherein each of said one or more apertures or holes is characterized by a width or diameter ranging of about 0.4 5 mm and the sum of the volume of said one or more apertures or holes is from about 1% to about 10% by total volume of said article.

* * * * *